(12) United States Patent
Keupp

(10) Patent No.: US 11,307,277 B2
(45) Date of Patent: Apr. 19, 2022

(54) MAGNETIZATION TRANSFER BASED METRIC FOR CHEMICAL EXCHANGE SATURATION TRANSFER MRI

(71) Applicant: KONINKLIJKE PHILIPS N.V., Eindhoven (NL)

(72) Inventor: Jochen Keupp, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 16/960,112

(22) PCT Filed: Jan. 2, 2019

(86) PCT No.: PCT/EP2019/050029
§ 371 (c)(1),
(2) Date: Jul. 6, 2020

(87) PCT Pub. No.: WO2019/137837
PCT Pub. Date: Jul. 18, 2019

(65) Prior Publication Data
US 2021/0063519 A1 Mar. 4, 2021

(30) Foreign Application Priority Data
Jan. 11, 2018 (EP) .................................... 18151154

(51) Int. Cl.
*G01R 33/56* (2006.01)
*A61B 5/055* (2006.01)
*G01R 33/483* (2006.01)

(52) U.S. Cl.
CPC .......... *G01R 33/5605* (2013.01); *A61B 5/055* (2013.01); *G01R 33/4838* (2013.01); *G01R 33/5608* (2013.01)

(58) Field of Classification Search
USPC ........................................................ 324/309
See application file for complete search history.

(56) References Cited

U.S. PATENT DOCUMENTS

2013/0147477 A1   6/2013   Singh et al.
2013/0166226 A1   6/2013   Lee et al.
(Continued)

OTHER PUBLICATIONS

Moritz Zaiss et al:"Relaxation-compensated CEST-MRI of the human brain at 7 T: Unbiased insight into NOE and amide signal changes in human glioblastoma",Neuroimage,vol. 112, Feb. 26, 2015 (Feb. 26, 2015), pp. 180-188.
(Continued)

*Primary Examiner* — Rodney E Fuller

(57) ABSTRACT

A medical analysis system (111) for processing magnetic resonance imaging (MRI), data (170) from a target volume (208) in a subject (218) includes a memory (107) for storing machine executable instructions; and a processor (103) for controlling the system (111). Execution of the machine executable instructions causes the processor (103) to: determine from the MRI data (103) chemical exchange saturation transfer (CEST) voxel values corresponding to a transfer of saturation between a predefined pool of protons and water protons, the pool of protons having a predefined chemical shift; and weight the CEST values in order to distinguish CEST values of fluid-rich tissues (507) from CEST values of solid tissues (505) in the target volume (208), wherein the fluid-rich tissue comprises an amount of fluid higher than a predefined minimum amount of fluid.

13 Claims, 4 Drawing Sheets

(56) References Cited

U.S. PATENT DOCUMENTS

| | | |
|---|---|---|
| 2013/0190601 A1 | 7/2013 | Alsop et al. |
| 2014/0062476 A1 | 3/2014 | Miyazaki et al. |
| 2016/0018496 A1 | 1/2016 | van Zijl et al. |
| 2020/0348382 A1* | 11/2020 | Keupp ............... G01R 33/5605 |

OTHER PUBLICATIONS

Moritz Zaiss et al: "Inverse Z-spectrum analysis for spillover-, MT-, and T 1-corrected steady-state pulsed CEST-MRI-application to pH-weighted MRI of acute stroke : Simple Spillover-, MT-, and T 1-Corrected CEST-MRI",NMR in Biomedicine.,vol. 27, No. 3,Jan. 3, 2014 (Jan. 3, 2014), pp. 240-252.

Jinyuan Zhou et al: "Using the amide proton signals of intracellular proteins and peptides to detect pH effects in MRI",Nature Medicine,vol. 9, No. 8, Aug. 1, 2003 (Aug. 1, 2003),pp. 1085-1090.

Jochen Keupp et al.: "Magnetization Transfer Ratio based Metric for APTw or CESTw MR I Suppressing Signal from Fluid Compartments—Initial Application to Glioblastoma Assessment",Proceedings of the International Society for Ma gnetic Resonance in Medicine, ISMRM,Joint Annual Meeting ISMRM-ESMRMB, Paris,France, Jun. 16-21, 2018,No. 3156, Jun. 1, 2018.

International Search Report and Written Opinion from PCT/EP2019/050029 dated Mar. 22, 2019.

Hye-Young Heo et al., Quantitative Assessment of Amide Proton Transfer (APT) and Nuclear Overhauser Enhancement (NOE) Imaging with Extrapolated Semisolid Magnetization Transfer Reference (EMR) Signals: II. Comparison of Three EMR Models and Application to Human Brain Glioma at 3Tesla; Magnetic Resonance in Med. 75 p. 1630-1639 (2016).

Hye-Young Heo et al., Quantitative Assessment of Amide Proton Transfer (APT) and Nuclear Overhauser Enhancement (NOE) Imaging with Extrapolated Semi-Solid Magnetization Transfer Reference (EMR) Signals: Application to a Rat Glioma Model at 4.7 Tesla; Magnetic Resonance in Med. 75 p. 137-149 (2016).

Yin Wu et al., pH-Sensitive Amide Proton Transfer Effect Dominates the Magnetization Transfer Asymmetry Contrast During Acute Ischemia—Quantification of Multipool Contribution to In Vivo CEST MRI; Magnetic Resonance in Med. 79 p. 1602-1608 (2017).

Jinyuan Zhou et al., APT-Weighted and NOE-Weighted Image Contrasts in Glioma with Different RF Saturation Powers Based on Magnetization Transfer Ratio Asymmetry Analyses; Magnetic Resonance in Med. 70 p. 320-327 (2013).

Guanshu Liu et al., NOrmalized MAgnetization Ratio (NOMAR) Filtering for Creation of Tissue Selective Contrast Maps; Magnetic Resonance in Med. 69 p. 516-523 (2013).

Ke Li et al., Influence of Water Compartmentation and Heterogeneous Relaxation on Quantitative Magnetization Transfer Imaging in Rodent Brain Tumors; Magnetic Resonance in Med. 76 p. 635-644 (2016).

Vitaliy Khlebnikov et al "Amide Proton Transfer (APT) Imaging of Brain Tumors at 7 T: The Role of Tissue Water T1-Relaxation Properties" Magnetic Resonance in Med. 77 p. 1525-1532 (2017).

Zhou J, et al "Using the amide proton sig-nals of intra¬cellular proteins and peptides to detect pH effects in MRI" Nature Medicine 2003; 9:1085.

Jones CK, Schlosser MJ, Zijl PCM, Pomper MG, Golay X, Zhou J. Amide proton transfer imaging of human brain tumors at 3T. Magn Reson Med 2006; 56:585.

Zhou J, Tryggestad E, Wen Z, Lal B, Zhou T, Grossman R, Wang S, Yan K, Fu DX, Ford E, Tyler B, Blakeley J, Laterra J, van Zijl PCM. Differentiation between glioma and radiation necrosis using molecular magnetic resonance imaging of endogenous proteins and peptides. Nature Medi¬cine 2011; 17:130.

Jones CK, Polders D, Hua J, Zhu H, Hoogduin HJ, Zhou J, Luijten P, van Zijl PC. In vivo three-dimensional whole-brain pulsed steady-state chemical exchange saturation transfer at 7 T. Magn Reson Med. Jun. 2012;67(6):1579-89.

Liu D, Zhou J, Xue R, Zuo Z, An J, Wang DJ. Quantitative characterization of nuclear overhauser enhancement and amide proton transfer effects in the human brain at 7 tesla. Magn Reson Med. Oct. 2013;70(4):1070-81.

* cited by examiner

MAGNETIZATION TRANSFER BASED METRIC FOR CHEMICAL EXCHANGE SATURATION TRANSFER MRI

CROSS REFERENCE TO RELATED APPLICATIONS

This application is a U.S. national phase application of International Application No. PCT/EP2019/050029 filed on Jan. 2, 2019, which claims the benefit of EP Application Serial No. 18151154.4 filed on Jan. 11, 2018 and is incorporated herein by reference.

FIELD OF THE INVENTION

The invention relates to scanning imaging systems, in particular to a medical analysis system for processing magnetic resonance imaging, MRI, data for suppressing data originated from fluid-rich tissues.

BACKGROUND OF THE INVENTION

Conventional magnetic resonance imaging (MRI) contrasts are based on the spin relaxation rates of different body tissues under a static magnetic field and various radiofrequency (RF) pulses. Known contrasts depend on T1, T2, proton density (PD), and T2* weighting. In order to gain further information on the body's conditions, novel image contrasts have been introduced using new imaging techniques such as the amide proton transfer (APT) technique. The APT technique, further called APT-weighted (APTw) MRI, is for example used for MR-based molecular imaging of endogenous cytosolic proteins or peptides. It is based on the chemical exchange saturation transfer (CEST) effect and reflects protein concentrations as well as local pH via the exchange rate. While one important aim of APT MRI is to characterize malignant lesions, particularly in oncology, other tissue types may show hyper-intensity in APT images and may be confounded with malignant lesions. In particular, tissue compartments with a significant fluid content and often high protein content highlight on APT images. It is thus desirable to suppress the APT signal in those compartments in order to simplify and improve diagnostic reading.

SUMMARY OF THE INVENTION

Various embodiments provide for a method for processing MRI data, medical analysis system, and computer program product, as described by the subject matter of the independent claims. Advantageous embodiments are described in the dependent claims.

The present disclosure discloses a correction function (also referred to as metric) for APTw MRI or chemical exchange saturation transfer (CEST) MRI. It is using the magnetization transfer ratio (MTR) to suppress confounding signals of tissue compartments with significant fluid content (e.g. cysts, hemorrhage, CSF, edema, fluid parts of necrotic tissue etc.), that may be mistaken as malignant lesions in CEST MRI (e.g. APTw MRI). This may particularly be advantageous for oncology applications in the brain. The correction function is used to conserve numerical values of standard CEST values (e.g. APTw values) in solid tissues. The correction function is useful in applications of CEST MRI, when suppression of data from compartments with significant fluid content is desired.

In one aspect, the invention relates to a medical analysis system for processing MRI data from a target volume in a subject. The system comprises a memory for storing machine executable instructions; and a processor for controlling the system, wherein execution of the machine executable instructions causes the processor to: determine from the MRI data CEST voxel values (or CEST signals) corresponding to a transfer of saturation between a predefined pool of protons and water protons, the pool of protons having a predefined chemical shift; and weight the CEST values in order to distinguish CEST values of fluid-rich tissues from CEST values of solid tissues in the target volume, wherein the fluid-rich tissue comprises an amount of fluid higher than a predefined minimum amount of fluid.

The protons of the pool resonate at different frequencies than the water protons. With the CEST technique, magnetization is transferred from the pool of protons to water protons, such that the saturation effect (i.e., signal reduction) that was originally imposed on the pool of protons can instead be observed on water protons. The MRI data may be acquired by saturating the pool of protons and allowing magnetization to transfer between the pool of protons and water protons. The CEST values obtained from the MRI data may indicate the CEST contrast at one or more frequency offsets of the pool of protons. The number of frequency offsets may be determined depending on the saturation scheme to be analyzed. To derive the CEST values for an exchanging chemical compound, CEST measurements for at least two opposite spectral locations plus a reference scan (at a large frequency offset, e.g. $\Delta\omega_0 < -1000$ pm) may be required. For example, a seven-offset (1:$+\Delta\omega$, 2:$-\Delta\omega$, 3:$+\Delta\omega+\delta$, 4:$-\Delta\Omega-\delta$, 5:$+\Delta\omega-\delta$, 6:$-\Delta\omega+\delta$, 7:$\Delta\omega_0$) saturation scheme (N=6 offsets, and one reference scan $S_0$ at $\Delta\omega_0$) may be used in case of a pool of amide protons for acquiring APTw images of brain tumors in patients, where $\Delta\omega=3.5$ ppm (chemical shift of amides) and e.g. $\delta=0.8$ ppm for the purpose of magnetic field correction.

The terms "saturation transfer", "proton transfer", "chemical exchange", and "magnetization transfer" involve the same process according to which protons are transferred or exchanged among a pool of protons and water protons and thus carry over their nuclear spin magnetization state, which may be a saturated spin state in particular.

The weighting of the CEST values in order to distinguish CEST values of fluid-rich tissues from CEST values of solid tissues in the target volume may comprise rescaling, downscaling or suppression of CEST values in fluid-rich tissues.

The term "solid tissue" refers to a biological tissue in a subject that is not a body fluid or fluid-rich tissue. The solid tissue has a firm tissue consistency and is neither air-filled tissue nor a liquid (such as blood). The solid tissue may refer to tissue of the brain, liver, lung, kidney, prostate, pancreas, ovary, spleen and the like.

The term "fluid-rich tissue" refers to fluid-filled tissues having an amount of fluid that is higher than a predefined minimum amount of fluid [e.g. >70% (the predefined minimum amount of fluid is 70%) of total water concentration]. "Fluid-rich tissue" refers to a tissue with a large water concentration in the extracellular space (outside cells), like interstitial or plasma fluids, as well as cell-free fluid compartments (e.g. cerebrospinal fluid=CSF, cystic compartments or hemorrhage). The fluid-rich tissue may be a fluid-filled tissue. The fluid-rich tissue is different from the solid tissue.

The present system may enable an automatic suppression of CEST signals in the fluid-rich tissues. This may simplify and improve diagnostic reading of CEST MRI data.

According to one embodiment, the pool of protons is a pool of amide protons, wherein the CEST values are amide proton transfer weighted, APTw, values. In this embodiment, the CEST effect is based on amide protons such that the CEST signal that is detected reflects the APT effect. The amide protons resonate at a chemical shift of $\Delta\omega=3.5$ ppm from the water resonance frequency. The term "APT value" and "APTw value" may be used interchangeably herein.

According to one embodiment, the weighting is performed such that the CEST values within the fluid-rich tissues is downscaled while the CEST values remain unchanged for the solid tissues. This may enable a seamless integration of the present invention with existing systems i.e. the implementation of the present invention may be transparent to the user in that the user can still see the signal of solid tissues at the same level as standard methods. The present method may for example conserve numerical values of standard APTw values in solid tissues.

According to one embodiment, the MRI data, is acquired using predefined MRI sequences, wherein the MRI data comprises non-saturated data $S_0=S(\Delta\omega_0)$ at a large saturation frequency offset $\Delta\omega_0$ (e.g. $\Delta\omega_0<-1000$ pm) (or without RF saturation) and saturation transfer data at N saturation frequency offsets (MRI data comprising the saturation transfer data and non-saturated data is also referred to as Z-spectrum), wherein $N\geq2$, wherein the weighting comprises: performing a quantitative tissue scoring using a subset of the saturation transfer data (or at least part of the saturation transfer data) and the non-saturated data in order to assess fluid content and solid tissue content at each voxel in the MRI data, generating a correction function using results of the scoring, and using the correction function to weight the CEST value of each voxel.

The subset of the saturation transfer data, used for scoring of fluid contents in order to generate the correction function, comprises saturation transfer data at N2 saturation frequency offsets, wherein $N2\leq N$.

The quantitative scoring of fluid contents scales or correlates with fluid contents but is not required to be a direct measure of fluid concentrations. This embodiment may enable an accurate classification of the fluid content which may thus improve the determination of CEST contrast in accordance with the present disclosure. Furthermore, an advantage of the disclosed metric may reside in the fact that no extra acquisition time may be needed, because the correction function can be computed from the saturation transfer data also required for standard CEST MRI (e.g. the MRI data used for computing the CEST values may be used to determine the correction function).

The N2 saturation frequency offsets ($N2\geq2$) used for generating the correction function may or may not be the same N3 ($2\leq N3\leq N$) frequency offsets that are used to determine CEST values, both taken from the acquired Z-spectrum with N different frequency offsets. The N2 frequency offsets for fluid correction may be chosen symmetrically around the water resonance frequency. From practical and scan time efficiency point of view it may be advantageous to derive the correction function and the CEST values from the same frequency offsets, which allows to minimize the number N of saturation frequency offsets that need to be acquired as MRI data.

According to one embodiment, the execution of the machine executable instructions further causes the processor to generate from the subset of the saturation transfer data (N2), and the non-saturated data $S_0$, magnetization transfer ratios, MTRs, for each voxel at N2 saturation frequency offsets, wherein $2\leq N2\leq N$. Subsequently combine the N2 MTRs for each voxel, wherein the quantitative tissue scoring is performed using the combined MTRs. The MTR at a given frequency offset $\Delta\omega$ is defined as follows: $MTR=1-S(\Delta\omega)/S_0$, where $S(\Delta\omega)$ is the signal amplitude obtained from the saturation transfer data and $S_0$ is the non-saturated reference signal. The combination of the MTRs may provide a reliable discriminating metric for distinguishing between image data of fluid-rich tissues and solid tissues. For example, the spectral average of MTRs provides the overall percent level of saturation transfer in each voxel, which is large for solid tissues but small for fluid-rich tissues.

According to one embodiment, the combined MTR for a given voxel is a weighted sum of the N2 MTRs of the given voxel. The weighted sum may be the average or weighted average of the N2 MTRs. Using the weighted sum may enable to control the correction process of the present disclosure based on the frequencies being used. For example, the N2 MTRs of the sum may be weighted depending on the respective frequency offset values.

According to one embodiment, using the correction function to weight the CEST values comprises multiplying a correction factor $CF=\varepsilon\times(MTR(+\Delta\omega_c)+MTR(-\Delta\omega_c))$ with CEST values, wherein $\pm\Delta\omega_c$ are the saturation frequency offsets, which corresponds to $N2=2$ MTRs used for the correction function in this embodiment. $\varepsilon$ is a factor that is determined such that the application of the correction factor results in the CEST values within the fluid-rich tissues being rescaled while the CEST values remain unchanged for the solid tissues. For $N2>2$ MTRs used, the correction factor CF may be defined as $$CF = \varepsilon \times \frac{2}{N2}\Sigma_{\delta\omega\in\{\Delta\omega_1,\Delta\omega_2,...\}}^{N2}MTR[\delta\omega].$$

According to one embodiment, the correction function is used for weighting (e.g. downscaling of CEST values in fluid-rich areas) by multiplying a correction factor with the CEST values: $CEST_{cf}(x)=CF*CEST(x)$.

In another example, the correction factor CF may be chosen such that operations other than the multiplication may be used to apply CF to CEST values:

$CEST_{cf}(x)=F[CF;CEST(x)]$ with the correction function $F[;]$.

According to one embodiment, the MRI data comprises saturation transfer data at N saturation frequency offsets and non-saturated MRI data of the target volume, the execution of the machine executable instructions further causes the processor to generate from a subset of the saturation transfer data and the non-saturated MRI data magnetization transfer ratios, MTRs, for each voxel at N3 saturation frequency offsets, wherein $N3\leq N$, wherein the CEST values being obtained by an analysis of the distribution of MTRs in comparison to a distribution (e.g. a fitted model of the MT background) which is symmetric with respect to the water resonance frequency. The subset of the saturation transfer data, used for determining the CEST values, comprises saturation transfer data at N3 saturation frequency offsets wherein $2\leq N3\leq N$. The subset of saturation data used for determining the CEST values may or may not be the same as the subset of the saturation transfer data used for scoring of fluid contents in order to generate the correction function.

According to one embodiment, the CEST value of a given voxel is obtained by a magnetization transfer asymmetry analysis ($MTR_{asym}$) which is the difference between the MTRs of the given voxel at two frequency offsets being symmetrically positioned on opposite sides of the water resonance frequency—the two frequencies corresponding to the chemical shift of the pool of protons of interest and its negation.

According to one embodiment, the MRI data comprises saturation transfer data at multiple saturation frequency offsets having a predefined chemical shift difference with respect to the water resonance frequency. Preferably, all saturation frequency offsets may at least be 1 ppm from the water resonance frequency; otherwise CEST values from fluid-rich tissues may not be sufficiently suppressed, because below 1 ppm direct water saturation is occurring on fluids. In one example for APTw MRI, a saturation frequency offset $\Delta\omega_c$ for fluid correction is favorably chosen at 3.5 ppm, the same as used for calculation of APTw values, which is a frequency area with substantial MTR differences between fluid and solid compartments and provides a good separation of fluid and solid compartments. In one example, the saturation frequency offsets have a predefined chemical shift difference with respect to the water resonance frequency that is smaller than a predefined maximum shift. Limiting the shifts to small values (e.g. 1 . . . 5 ppm) using the predefined maximum shift may be advantageous because the smaller the offset, the higher the expected signal changes between fluid and solid compartments.

According to one embodiment, the saturation transfer data is corrected for B0 field inhomogeneity before being used (e.g. before the CEST values are computed and before the correction factor is determined). The consequence of B0 field inhomogeneity is a position-dependent shift of the entire Z-spectrum representing the saturation transfer data, e.g. $S(\Delta\omega)$ is no longer at their assumed position, making the calculation of CEST values inaccurate. The B0 field inhomogeneity information may be derived from intrinsically acquired B0 information from the same Z-spectrum acquisition or by separately acquired B0 information (e.g. gradient echo B0 field maps, WASSR maps or the like).

For example, the correction for the artifacts that may be caused by B0 inhomogeneity, may comprise the acquisition of extra MRI data for extra offsets around the $\pm\Delta\omega$. For example, a seven-offset (1:$+\Delta\omega$, 2:$-\Delta\omega$, 3:$+\Delta\omega+\delta$, 4:$-\Delta\omega-\delta$, 5:$+\Delta\omega-\delta$, 6:$-\Delta\omega+\delta$, 7:$\Delta\omega_0$) saturation scheme (N=6) may be used with $\delta$ specifying the extra offsets for the purpose of magnetic field correction, e.g. $\delta=0.8$ ppm. With the additional frequency offsets measured on each side and a B0 map, the actual signal at $\pm 3.5$ ppm may be deduced (e.g. by a Lagrange interpolation for the Z-spectrum) and then used to compute the CEST values, for example using $MTR_{asym}$.

According to one embodiment, the fluid-rich tissue comprises at least one of the following tissue types: a cyst, hemorrhage, cerebrospinal fluid (SF), edema, inflamed tissue, fluid parts of necrotic tissue or other fluid-rich tissues.

In another aspect, the invention relates to a method for processing magnetic resonance imaging MRI data from a target volume in a subject. The method comprises: determining from the MRI data chemical exchange saturation transfer, CEST, voxel values corresponding to a transfer of saturation between a predefined pool of protons and water protons, the pool of protons having a predefined chemical shift; weighting the CEST values in order to distinguish CEST values of fluid-rich tissues from CEST values of solid tissues in the target volume, wherein the fluid-rich tissue comprises an amount of fluid higher than a predefined minimum amount of fluid.

The method may automatically be performed e.g. upon determining or receiving the CEST voxel values.

In another aspect, the invention relates to a computer program product comprising machine executable instructions for execution by a processor, wherein execution of the machine executable instructions causes the processor to the methods of any of the preceding embodiments.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

In the following, like numbered elements in the figures are either similar elements or perform an equivalent function. Elements which have been discussed previously will not necessarily be discussed in later figures if the function is equivalent.

Various structures, systems and devices are schematically depicted in the figures for purposes of explanation only and so as to not obscure the present invention with details that are well known to those skilled in the art. Nevertheless, the attached figures are included to describe and explain illustrative examples of the disclosed subject matter.

Figure 1:
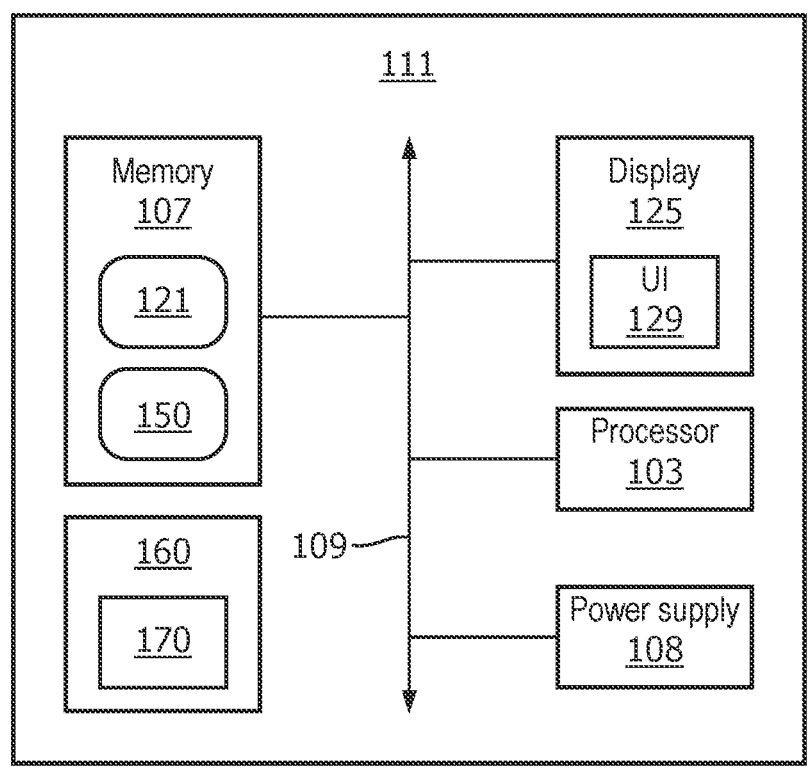
FIG. 1 is a schematic diagram of a medical analysis system.

FIG. 1 is a schematic diagram of a medical analysis system 111. The medical analysis system 111 comprises a processor 103, a memory 107 each capable of communicating with one or more components of the system 111. For example, components of the medical analysis system 111 are coupled to a bidirectional system bus 109.

It will be appreciated that the methods described herein are at least partly non-interactive, and automated by way of computerized systems. For example, these methods can further be implemented in software 121, (including firmware), hardware, or a combination thereof. In exemplary embodiments, the methods described herein are implemented in software, as an executable program, and is executed by a special or general-purpose digital computer, such as a personal computer, workstation, minicomputer, or mainframe computer.

The processor 103 is a hardware device for executing software, particularly that stored in memory 107. The processor 103 can be any custom made or commercially available processor, a central processing unit (CPU), an auxiliary processor among several processors associated with the medical analysis system 111, a semiconductor based microprocessor (in the form of a microchip or chip set), a macroprocessor, or generally any device for executing software instructions. The processor 103 may control the operation of a scanning imaging system to which the medical analysis system 111 is connected.

The memory 107 can include any one or combination of volatile memory elements (e.g., random access memory (RAM, such as DRAM, SRAM, SDRAM, etc.)) and non-volatile memory elements (e.g., ROM, erasable programmable read only memory (EPROM), electronically erasable programmable read only memory (EEPROM), programmable read only memory (PROM). Note that the memory 107 can have a distributed architecture, where various components are situated remote from one another, but can be accessed by the processor 103. Memory 107 may store an instruction or data related to at least one other constituent element of the system 111.

The medical analysis system 111 may further comprise a display device 125 which displays characters and images and the like e.g. on a user interface 129. The display device 125 may be a touch screen display device.

The medical analysis system 111 may further comprise a power supply 108 for powering the medical analysis system 111. The power supply 108 may for example be a battery or an external source of power, such as electricity supplied by a standard AC outlet.

Figure 3:
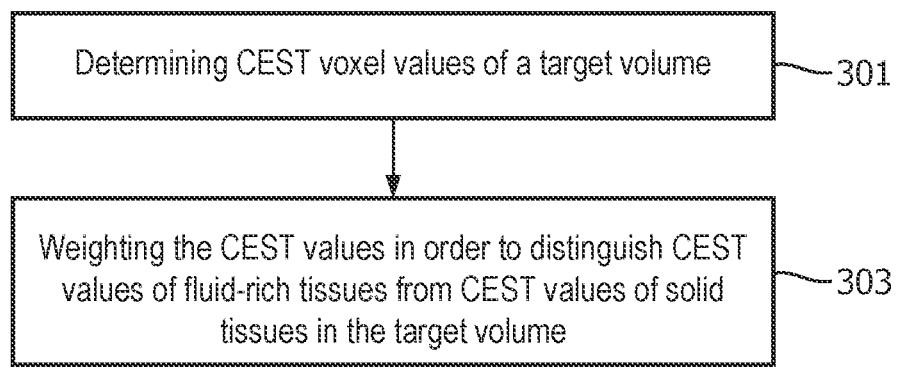
FIG. 3 is a flowchart of a method for processing MRI data.

The medical analysis system 111 may be configured to connect to a scanning imaging system (not shown) such as MRI, CT and PET-CT imagers. The connection between the medical analysis system 111 and the scanning imaging system may for example comprise a BUS Ethernet connection, WAN connection, Internet connection etc. The medical analysis system 111 and the scanning imaging system may or may not be an integral part. In other terms, the medical analysis system 111 may or may not be external to the scanning imaging system. The scanning imaging system comprises components that may be controlled by the processor 103 in order to configure the scanning imaging system. The configuration of the scanning imaging system may enable the operation of the scanning imaging system. The operation of the scanning imaging system may for example be automatic. FIG. 3 shows an example of components of the scanning imaging system being an MRI system. In one example, the scanning imaging system may be configured to provide output data such as images in response to a specified measurement.

The processor 103 may be adapted to receive information from the scanning imaging system in a compatible digital form so that such information may be displayed on the display device 125. Such information may include operating parameters, alarm notifications, and other information related to the use, operation and function of the scanning imaging system 101.

The memory 107 may further comprise a CEST analysis component 150 for processing MRI data 170 from a target volume in a subject. The MRI data 170 may be stored in a storage device 160 of the system 111. The CEST analysis component 150 may or may not be part of software component 121. For example, the CEST analysis component 150 may be configured to perform at least part of the present method.

Figure 2:
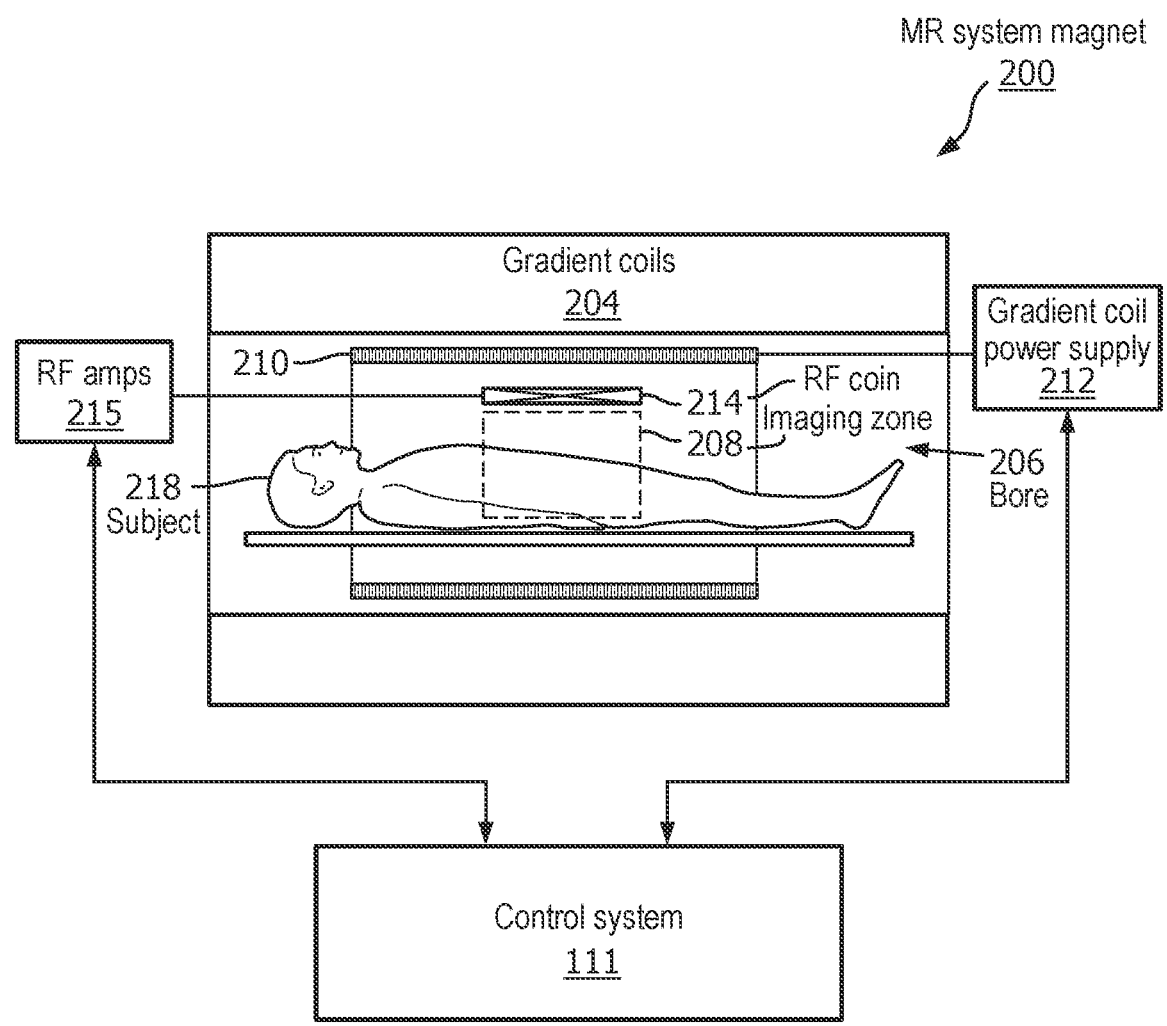
FIG. 2 shows a cross-sectional and functional view of an MRI system.

FIG. 2 illustrates a magnetic resonance imaging system 200. The magnetic resonance imaging system 200 comprises a magnet 204. The magnet 204 is a superconducting cylindrical type magnet with a bore 206 in it. The use of different types of magnets is also possible; for instance, it is also possible to use both a split cylindrical magnet and a so called open magnet. A split cylindrical magnet is similar to a standard cylindrical magnet, except that the cryostat has been split into two sections to allow access to the iso-plane of the magnet. Such magnets may for instance be used in conjunction with charged particle beam therapy. An open magnet has two magnet sections, one above the other with a space in-between that is large enough to receive a subject 218 to be imaged, the arrangement of the two sections area similar to that of a Helmholtz coil. Inside the cryostat of the cylindrical magnet there is a collection of superconducting coils. Within the bore 206 of the cylindrical magnet 204 there is an imaging zone or volume or anatomy 208 where the magnetic field is strong and uniform enough to perform magnetic resonance imaging.

Within the bore 206 of the magnet there is also a set of magnetic field gradient coils 210 which is used during acquisition of magnetic resonance data to spatially encode magnetic spins of a target volume within the imaging volume or examination volume 208 of the magnet 204. The magnetic field gradient coils 210 are connected to a magnetic field gradient coil power supply 212. The magnetic field gradient coils 210 are intended to be representative. Typically, magnetic field gradient coils 210 contain three separate sets of coils for the encoding in three orthogonal spatial directions. A magnetic field gradient power supply supplies current to the magnetic field gradient coils. The current supplied to the magnetic field gradient coils 210 is controlled as a function of time and may be ramped or pulsed.

MRI system 200 further comprises an RF coil 214 at the subject 218 and adjacent to the examination volume 208 for generating RF excitation pulses. The RF coil 214 may include for example a set of surface coils or other specialized RF coils. The RF coil 214 may be used alternately for transmission of RF pulses as well as for reception of magnetic resonance signals e.g., the RF coil 214 may be implemented as a transmit array coil comprising a plurality of RF transmit coils. The RF coil 214 is connected to one or more RF amplifiers 215.

The magnetic field gradient coil power supply 212 and the RF amplifier 215 may be connected to medical analysis system 111 e.g. they may be connected to a hardware interface of medical analysis system 111. The memory 107 of medical analysis system 111 may for example comprise a control module. The control module contains computer-executable code which enables the processor 103 to control the operation and function of the magnetic resonance imaging system 200. It also enables the basic operations of the magnetic resonance imaging system 200 such as the acquisition of magnetic resonance data. The control module may for example be part of the CEST analysis component 150.

The MRI system 200 may be configured to acquire MRI data 170 from the target volume 208. The MRI data 170 may be acquired at a predefined slice with multiple voxels. The MRI data may be used to quantify CEST effect by determining CEST values for voxels in the MRI data using the MRI data. The CEST effect may be expressed in terms of a signal reduction with respect to the signal without saturation, $S_0$. The MRI data 170 may for example comprise saturation transfer data at N saturation frequency offsets, wherein N>=2. The MRI data 170 may further comprise non-saturated data.

The saturation transfer data at a given frequency offset $\Delta\omega$ may for example be acquired using a MRI sequence containing a selective saturation RF pulse followed by a excitation RF pulse to control the MRI system 200 to selectively excite and saturate a predefined pool of protons at the given frequency offset. The MRI sequence may be a TSE sequence. The pool of protons may for example comprise amide (NH) protons and the given frequency offset $\Delta\omega$ may be $\Delta\omega=\pm3.5$ ppm with respect to the water resonance frequency. In this case, the CEST effect may be an amide proton transfer APT effect.

The non-saturated data may for example be obtained with a largely detuned saturation frequency offset (e.g. the frequency offset may be $\Delta\omega_0 < -1000$ ppm) in the MRI sequence or without RF saturation.

The CEST effect may be quantified using known techniques involving an analysis of the distribution of the saturation transfer ratios, MTR. CEST values may be determined using a subset of saturation transfer data of the MRI data 170. The subset of the saturation transfer data comprises saturation transfer data at N3 frequency offsets, where N3≤N.

For example, CEST value of a given voxel x may be defined as follows for N3=2:

$$CEST(x) = MTR_{asym} = (S(-\Delta\omega) - S(+\Delta\omega))/S_0 \quad \text{Eq.1}$$

where $S(-\Delta\omega)$ and $S(+\Delta\omega)$ are the signal amplitudes obtained from the saturation transfer data. So is the signal amplitude obtained from the non-saturated data without selective saturation RF pulse. The $MTR_{asym}$ of equation Eq.1 may be written as follows: $CEST = MTR_{asym} = MTR(+\Delta\omega) - MTR(-\Delta\omega)$, where $MTR(\Delta\omega)$ is the magnetization transfer ratio MTR for frequency offset $\Delta\omega$:

$$MTR(\Delta\omega) = 1 - S(\Delta\omega)/S_0 \quad \text{Eq.2}$$

In another example, CEST values may be determined by fitting a model of the magnetization transfer to the Z-spectral data based on selected spectral regions that are not influenced by saturation transfer effects of the specific pool(s) of protons used for CEST MRI. Ideally, these selected spectral regions for fitting only show magnetization transfer effects, from predefined pools of protons such as backbone protons or protons in cell membranes/fiber structures/myelin, which is called magnetization transfer background. CEST values are then deduced from the difference of the Z-spectral data to the fitted curve at the nominal chemical shift $\Delta\omega$ e.g. +3.5 ppm for APT.

FIG. 3 is a flowchart of a method for processing the MRI data 170 from target volume 208. The target volume may for example comprise a brain, liver, lung, kidney, prostate, pancreas, ovary, spleen or the like.

In step 301, CEST voxel values may be determined from the MRI data 170. The CEST voxel values correspond to a transfer of saturation between a predefined pool of protons and water protons. The protons of the pool have a predefined chemical shift relative to the water resonance frequency. For example, the pool of protons may comprise amide protons having. This step may result in a CEST value, CEST(x), for each voxel x of the MRI data 170. The CEST values may be determined as described with reference to FIG. 2.

In step 303, the values CEST(x) may be weighted in order to distinguish CEST values of fluid-rich tissues from CEST values of solid tissues in the target volume 208. Each fluid-rich tissue of the fluid-rich tissues comprises an amount of fluid higher than a predefined minimum amount of fluid a described above. This step may result in a weighted or corrected CEST value, $CEST_{cf}(x)$, for each voxel x of the MRI data 170 (where "cf" stands for corrected for fluids). For data obtained at the two frequency offsets $\Delta\omega = \pm 3.5$ ppm, CEST(x) would refer to APT(x) and $CEST_{cf}(x)$ would refer to $APT_{cf}(x)$.

The weighting in step 303 may comprise rescaling, downscaling or suppressing of CEST values in fluid-rich tissues. The weighting may be performed using a subset of the saturation transfer data of the MRI data 170. The subset of the saturation transfer data comprises saturation transfer data at N2 frequency offsets, wherein N2≤N. For example, each voxel of MRI data may be associated with a Z-spectrum indicative of the signal amplitudes $S(\Delta\omega)$ at N2 saturation frequency offsets $\Delta\omega$, where N2>=2. The N2 saturation frequency offsets may be smaller or equal than the N saturation frequency offsets of the MRI data 170. The N2 saturation frequency offsets used for generating the correction function may or may not be the same N3 (N3≤N) frequency offsets that are used to determine CEST values.

Using at least part of the Z-spectrum, a quantitative tissue scoring may be performed in order to assess fluid content and solid tissue content at each voxel in the MRI data. For example, by comparing the values of the Z-spectrum of a fluid-rich voxel with a Z-spectrum of a solid tissue voxel, a correction function may be generated that can be applied to the values CEST(x) such that CEST(x) of voxels of the fluid-rich tissues are rescaled (e.g. downscaled) while the CEST(x) of voxels of the solid tissues remain unchanged. The weighting step 303 may comprise applying the correction function on the CEST values obtained in step 301 in order to obtain the values $CEST_{cf}(x)$.

Figure 4:
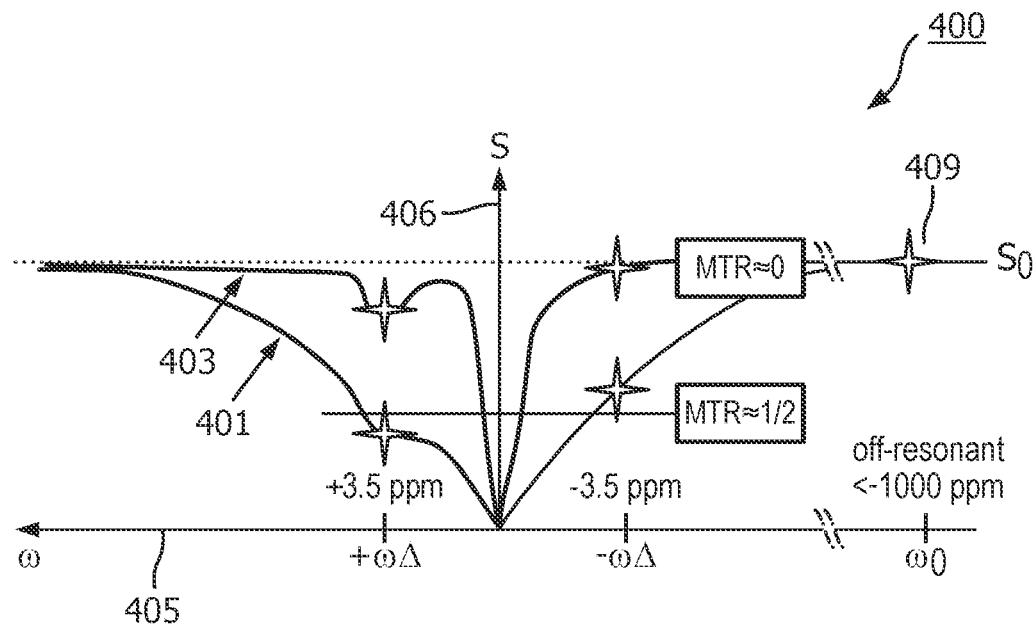
FIG. 4 is a plot of Z-spectrum for a voxel of a solid tissue and a voxel of a fluid-rich tissue.

FIG. 4 depicts a plot 400 of a Z-spectrum 401 for a voxel of a solid tissue and a Z-spectrum 403 for a voxel of fluid-rich tissue. Z-spectrum 401-403 encompass the water resonance frequency 407. FIG. 4 describes an example method for determining a correction function or a metric for performing the weighting step 303 for both N2=2 and N2>=2.

The Z-spectrum 401-403 may be selected among predefined Z-spectrum of voxels of a predefined slice of the target volume 208. The predefined Z-spectrum may be obtained by selectively exciting and saturating exchangeable amide protons in the target volume 208 at multiple frequency offsets $\Delta\omega = \pm 3.5$ ppm as indicated on the x-axis 405 of the plot 400 (y-axis 406 refers to signal amplitudes $S(\Delta\omega)$). This may be performed using the following MRI sequence settings: a saturation time Tsat=2 seconds, saturation RF field $B1_{rms} = 2 \mu T$ and $\Delta\omega = \pm 3.5$ ppm. The predefined Z-spectrum may for example be part of the MRI data 170. The plot 400 further indicates the non-saturated signal level $S_0$ 409.

Using the signal amplitudes $S(\Delta\omega)$ of the Z-spectrum 401-403, the MTR may be determined for each frequency offset $\Delta\omega$ using equation Eq.2. Plot 400 indicates for fluid-rich tissue of Z-spectrum 403 that the MTR at $\Delta\omega = \pm 3.5$ ppm is almost equal to 0. This indicates that the reduction of the signal amplitudes of Z-spectrum 403 with respect to the non-saturated signal $S_0$ is almost equal to zero at $\Delta\omega = \pm 3.5$ ppm. However, in the solid tissue, the signal at $\Delta\omega = \pm 3.5$ ppm is typically reduced with respect to $S_0$ by a factor of 2, so that $MTR(\pm 3.5 \text{ ppm}) \approx \frac{1}{2}$, as shown in FIG. 4. Thus, MTR for fluid-rich tissues is significantly lower as compared to solid tissues.

By comparting the MTR of the Z-spectrum 401 and 403, scoring information may be determined or deduced. For example, the scoring information may indicate that the sum $MTR(+\Delta\omega) + MTR(-\Delta\omega) = MTR(+3.5 \text{ ppm}) + MTR(-3.5 \text{ ppm}) \approx \frac{1}{2} + \frac{1}{2} = 1.0$ for the Z-spectrum 401 is 1 while it is different from 1 for the Z-spectrum 403.

Using the scoring information, a metric or correction function may be generated in order to weight the values CEST(x). For example, a correction factor $CF = \varepsilon \times (MTR(-\Delta\omega) + MTR(+\Delta\omega))$ may be used to weight the values CEST (x) determined in step 301. The weighted CEST values referred to as $CEST_{cf}(x)$ may be defined as follows:

$$CEST_{cf}(x) = MTR_{asym,cf} = MTR_{asym} \times \varepsilon \times (MTR(-\Delta\omega) + MTR(+\Delta\omega)) \quad \text{Eq.3}$$

The weighting ε is adjusted once for the specific settings, protocol or application being used to get the MRI data 170, to yield similar CEST values (CEST(x)=CEST$_{cf}$(x)) in solid tissues as for standard values e.g. the standard values may be the CEST values obtained in step 301. For the above described settings (i.e. saturation time T$_{sat}$=2 seconds, saturation RF field B1$_{rms}$=2 µT and Δω≈+3.5 ppm) the weighting is chosen as ε=1.0 because as described above the sum MTR(+Δω)+MTR(−Δω) is equal to 1 and thus the application of CF=ε×(MTR(−Δω)+MTR(+Δω)) with ε=1.0 results in the CEST values within the fluid-rich tissues being rescaled while the CEST values remain unchanged for the solid tissues.

The MTR$_{asym,cf}$ values of equation Eq.3 can be written as (e.g. for practical calculations) as follows:

$$MTR_{asym,cf} = MTR_{asym} \times \varepsilon \times \left(2 - \frac{S[\Delta\omega] + S[-\Delta\omega]}{S_0}\right),$$

Or $$MTR_{asym,cf} = \varepsilon \times (MTR^2[+\Delta\omega] - MTR^2[-\Delta\omega]).$$

The correction function thus derived for data (e.g. the MRI data 170) acquired at two frequency offsets Δω=±3.5 ppm using the above settings consists of multiplying the values CEST(x) (e.g. of step 301) with the correction factor CF=ε×(MTR(−Δω)+MTR(+Δω))

The correction function described above (for N2=2) may be used to define the correction function for N2≥2 that enables a general fluid correction of CEST values. The correction function for N2≥2 may be defined as follows:

$$MTR_{asym,cf} = MTR_{asym} \times \varepsilon \times \frac{2}{N2} \Sigma_{\delta\omega \in \{\Delta\omega_1, \Delta\omega_2, \ldots\}}^{N2} MTR[\delta\omega], \quad \text{Eq.4}$$

where N2 may be a predefined number of saturation frequency offsets {Δω$_1$, Δω$_2$, ... }, where the last term of equation Eq.4 is a weighted sum of N2 MTRs. The weighted sum relates to the overall percent level of magnetization transfer in each voxel, which is large for solid tissues but small for fluid-rich tissues. The weighted sum may be the average of MTRs at two or more saturation frequency. This may reduce the influence of actual APT (or fat/NOE effects) on the weighting process.

As described above, ε=1.0 is a favorable choice for scan time-efficient APT imaging with the abovementioned settings and N2=2, Δω$_1$=+3.5 ppm and Δω$_2$=−3.5 ppm. For N3=2 and two frequency offsets Δω=3.5 ppm, CEST(x) refers to APTw(x) (CEST(x)=APTw(x)). In case, the saturation effect is lower for a given protocol setting, ε can be tuned (e.g. increased) such that in solid tissues ε×(MTR[Δω$_1$]+MTR[Δω$_2$])≈1.0, or $$\left(\varepsilon \times \frac{2}{N2} \Sigma_{\delta\omega \in \{\Delta\omega_1, \Delta\omega_2, \ldots\}}^{N2} MTR[\delta\omega]\right) \approx 1.0 \text{ for } N2 \geq 2.$$

For determining the correction function, all Δω$_i$ may preferably be chosen at least 1 ppm from the water resonance frequency; otherwise fluid tissues may not be sufficiently suppressed. If the Z-spectral protocol does not contain large spectral offsets, it may be preferred to re-use existing spectral data (e.g. Δω=±3.5 ppm for APT) for scan time efficiency.

Figure 5A:
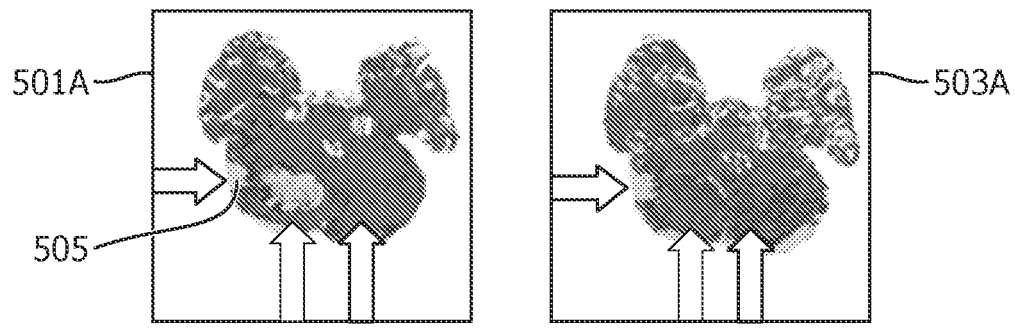
FIGS. 5A-C depict maps of APTw values and corresponding maps of weighted or corrected APTw values including correction (weighting) for fluid-rich tissues for selected tumor cases.
Figure 5B:
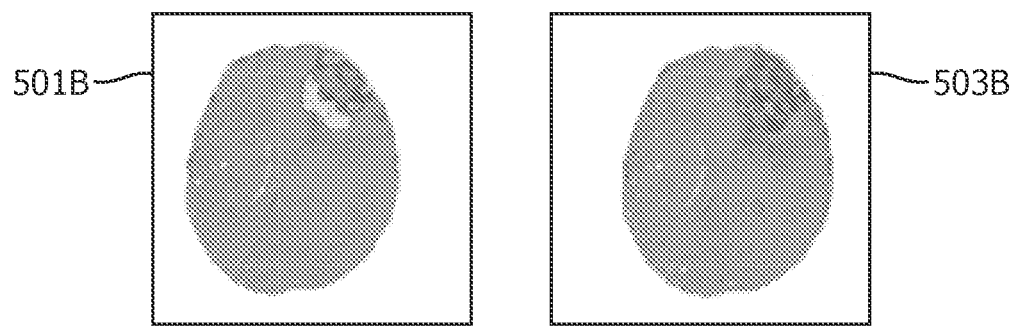
Figure 5C:
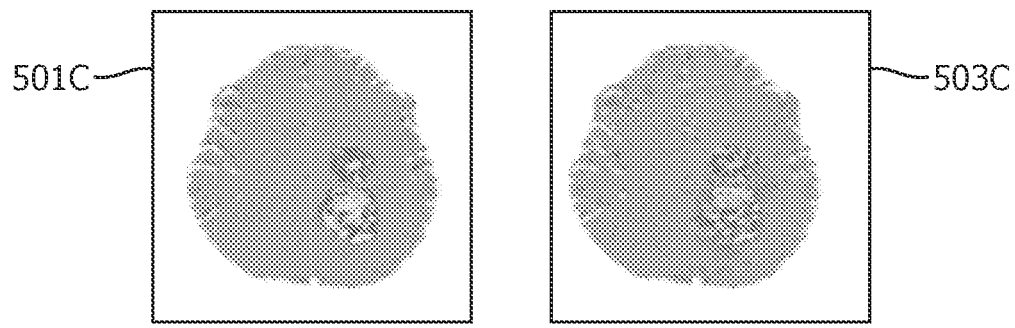

FIGS. 5A-C depict maps of APT$_w$(x) and APT$_{cf}$(x) that result from the application of the present method for brain tumor imaging.

In these examples of FIGS. 5A-C, the present method has been built in offline processing software and tested on retrospective data obtained for human brain tumor imaging with standard APT acquisition protocols (e.g. saturation time T$_{sat}$=2 seconds, saturation RF field B1$_{rms}$=2 µT, Δω=+3.5 ppm, 2D fast spin echo acquisition). The MTR$_{asym,cf}$ are computed using equation Eq.3 with ε=1.0.

FIGS. 5A-C depict maps 501A-501C of APTw(x) for selected tumor cases. FIG. 5A comprises a map 501A of values APT$_w$(x) representing the tumor case with cystic tissue 507 and brain metastasis 505. FIG. 5B comprises a map 501B of values APT$_w$(x) representing the tumor case with partial fluid content of brain metastases. FIG. 5C comprises map 501C of values APT$_w$(x) representing the tumor case with no fluid content of brain metastases.

The weighting of the APT$_w$(x) of maps 501A-C in accordance with the present method using equation Eq.3 results in the weighted APT$_{cf}$ maps 503A-C respectively, wherein each weighted APT$_{cf}$ map comprises values APT$_{cf}$(x) that results from the weighting of the respective values APT$_w$(x).

As indicated in FIGS. 5A-C, fluid components are clearly suppressed, while the metastasis contrast is maintained. For example, in FIG. 5A the cystic tissue 507 is suppressed (cf. contrast change between 501A and 503A) while the brain metastasis 505 contrast is maintained. The values of the maps of FIGS. 5A-C varies between −5% . . . +5% of MTR$_{asym}$ and MTR$_{asym,cf}$.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a 'circuit', 'module' or 'system'. Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

A 'computer memory' or 'memory' is an example of a computer-readable storage medium. A computer memory is any memory which is directly accessible to a processor. A 'computer storage' or 'storage' is a further example of a computer-readable storage medium. A computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising 'a processor' should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object-oriented programming language such as Java, Smalltalk, C++ or the like and conventional procedural programming languages, such as the 'C' programming language or similar programming languages and compiled into machine executable instructions. In some instances, the computer executable code may be in the form of a high-level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device'. A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word 'comprising' does not exclude other elements or steps, and the indefinite article 'a' or 'an' does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 medical system
101 scanning imaging system
103 processor
107 memory
108 power supply
109 bus
111 control system
121 software
125 display
129 user interface
150 CEST analysis component
200 magnetic resonance imaging system
204 magnet
206 bore of magnet
208 imaging zone
210 magnetic field gradient coils
212 magnetic field gradient coil power supply
214 radio-frequency coil
215 RF amplifier
218 subject
301-303 method steps
400 plot
401 Z-spectrum
403 Z-spectrum
405 x-axis
406 y-axis
407 water resonance frequency.

The invention claimed is:

1. A medical analysis system for processing magnetic resonance imaging (MRI) data from a target volume in a subject, the target volume includes fluid-rich tissues and solid tissues, wherein the fluid-rich tissue includes an amount of fluid higher than a predefined minimum amount of fluid, the system comprising:
   a memory configured to store machine executable instructions; and a processor for controlling the system, wherein execution of the machine executable instructions causes the processor to:
   determine from the MRI data chemical exchange saturation transfer, CEST, voxel values corresponding to a transfer of saturation between a predefined pool of protons and water protons, the pool of protons having a predefined chemical shift;
   weight the CEST values in order to distinguish CEST values of fluid-rich tissues from CEST values of solid tissues in the target volume, the MRI data being acquired using predefined MRI sequences, wherein the MRI data comprises non-saturated data at a predefined large saturation frequency offset or without RF saturation and saturation transfer data at N saturation frequency offsets, wherein N>=2, wherein the weighting comprises: performing a quantitative tissue scoring using a subset of the saturation transfer data comprising N2 saturation frequency offsets and the non-saturated data in order to assess fluid content and solid tissue content at each voxel in the MRI data, generating a correction function using results of the scoring, and using the correction function to weight the CEST value of each voxel, wherein using the correction function to weight the CEST values comprises multiplying a correction factor CF=ε×(MTR(+Δω$_c$)+MTR(−Δω$_c$)) with CEST values, wherein ±Δω$_c$ are the saturation frequency offsets and ε is a factor that is determined such that the application of the correction factor results in the CEST values within the fluid-rich tissues being rescaled while the CEST values remain unchanged for the solid tissues.

2. The system of claim 1, wherein the proton pool comprises amide protons, wherein the CEST values are amide proton transfer weighted, APTw, values.

3. The system of claim 1, the weighting being performed such that the CEST values within the fluid-rich tissues are rescaled while the CEST values remain unchanged for the solid tissues.

4. The system of claim 1, the execution of the machine executable instructions further causes the processor to generate from the subset of the saturation transfer data and non-saturated data N2 magnetization transfer ratios, MTRs, for each voxel at N2 saturation frequency offsets, wherein N2≤N, and combine the N2 MTRs for each voxel, wherein the quantitative tissue scoring is performed using the combined MTRs.

5. The system of claim 4, wherein the combined MTR for a given voxel is a weighted sum of the N2 MTRs of the given voxel.

6. The system of claim 1, wherein the MRI data comprises saturation transfer data at N saturation frequency offsets and non-saturated MRI data of the target volume, the execution of the machine executable instructions further causes the processor to generate from a subset of the saturation transfer data and the non-saturated MRI data magnetization transfer ratios, MTRs, for each voxel at N3 saturation frequency offsets, wherein N3≤N, wherein the CEST values being obtained by an analysis of the distribution of MTRs in comparison to a distribution which is symmetric with respect to the water resonance frequency.

7. The system of claim 6, wherein the CEST value of a given voxel is obtained by a magnetic transfer asymmetry analysis, $MTR_{asym}$, which is the difference between the MTRs of the given voxel at two frequency offsets being symmetrically positioned on opposite sides of the water resonance frequency.

8. The system of claim 1, wherein the MRI data comprises saturation transfer data at multiple saturation frequency offsets having a predefined chemical shift difference with respect to the water resonance frequency.

9. The system of claim 1, wherein the saturation transfer data is corrected for B0 field inhomogeneity before the saturation transfer data being used.

10. The system of claim 1, wherein the fluid-rich tissue comprises at least one of the following tissue types: a cyst, hemorrhage, cerebrospinal fluid (CSF), edema, inflamed tissue, fluid parts of necrotic tissue or other fluid-rich tissues.

11. An MRI system comprising the medical analysis system of claim 1, and an acquisition component for acquiring the MRI data.

12. A method for processing magnetic resonance imaging MRI data from a target volume in a subject, the method comprising:
    determining from the MRI data chemical exchange saturation transfer, CEST, voxel values corresponding to a transfer of saturation between a predefined pool of protons and water protons, the pool of protons having a predefined chemical shift;
    weighting the CEST values in order to distinguish CEST values of fluid-rich tissues from CEST values of solid tissues in the target volume, wherein the fluid-rich tissue comprises an amount of fluid higher than a predefined minimum amount of fluid, the MRI data being acquired using predefined MRI sequences, wherein the MRI data comprises non-saturated data at a predefined large saturation frequency offset or without RF saturation and saturation transfer data at N saturation frequency offsets, wherein N>=2, wherein the weighting comprises: performing a quantitative tissue scoring using a subset of the saturation transfer data comprising N2 saturation frequency offsets and the non-saturated data in order to assess fluid content and solid tissue content at each voxel in the MRI data, generating a correction function using results of the scoring, and using the correction function to weight the CEST value of each voxel, wherein using the correction function to weight the CEST values comprises multiplying a correction factor $CF=\epsilon \times (MTR(+\Delta\omega_c)+MTR(-\Delta\omega_c))$ with CEST values, wherein $\pm\Delta\omega_c$ are the saturation frequency offsets and $\epsilon$ is a factor that is determined such that the application of the correction factor results in the CEST values within the fluid-rich tissues being rescaled while the CEST values remain unchanged for the solid tissues.

13. A computer program product comprising machine executable instructions stored on a non-transitory computer readable medium for execution by a processor, wherein execution of the machine executable instructions causes the processor to process magnetic resonance imaging MRI data from a target volume in a subject by:
    determining from the MRI data chemical exchange saturation transfer, CEST, voxel values corresponding to a transfer of saturation between a predefined pool of protons and water protons, the pool of protons having a predefined chemical shift; and weighting the CEST values in order to distinguish CEST values of fluid-rich tissues from CEST values of solid tissues in the target volume, wherein the fluid-rich tissue comprises an amount of fluid higher than a predefined minimum amount of fluid, the MRI data being acquired using predefined MRI sequences, wherein the MRI data comprises non-saturated data at a predefined large saturation frequency offset or without RF saturation and saturation transfer data at N saturation frequency offsets, wherein N>=2, wherein the weighting comprises: performing a quantitative tissue scoring using a subset of the saturation transfer data comprising N2 saturation frequency offsets and the non-saturated data in order to assess fluid content and solid tissue content at each voxel in the MRI data, generating a correction function using results of the scoring, and using the correction function to weight the CEST value of each voxel, wherein using the correction function to weight the CEST values comprises multiplying a correction factor $CF=\epsilon \times (MTR(+\Delta\omega_c)+MTR(-\Delta\omega_c))$ with CEST values, wherein $\pm\Delta\omega c$ are the saturation frequency offsets and $\epsilon$ is a factor that is determined such that the application of the correction factor results in the CEST values within the fluid-rich tissues being rescaled while the CEST values remain unchanged for the solid tissues.

* * * * *